United States Patent [19]

Mesch et al.

[11] 3,957,830

[45] May 18, 1976

[54] MANUFACTURE OF SUCCINIC ANHYDRIDE

[75] Inventors: Walter Mesch, Ruchheim; Arnold Wittwer, Ludwigshafen, both of Germany

[73] Assignee: BASF Aktiengesellschaft, Ludwigshafen (Rhine), Germany

[22] Filed: Mar. 17, 1975

[21] Appl. No.: 558,886

[52] U.S. Cl. .......................... 260/346.8 R; 203/15; 203/57; 203/60; 203/64
[51] Int. Cl.² ................................. C07D 307/60
[58] Field of Search ............ 260/346.8 R, 346.8 M; 230/57, 60, 64, 15

[56] References Cited
FOREIGN PATENTS OR APPLICATIONS
1,386,278  12/1962  France
1,217,900  5/1960  France

*Primary Examiner*—Henry R. Jiles
*Assistant Examiner*—Bernard I. Dentz
*Attorney, Agent, or Firm*—Johnston, Keil, Thompson & Shurtleff

[57] ABSTRACT

Process for the manufacture of succinic anhydride by eliminating water from succinic acid using a chemically inert hydrophilic solvent which does not form an azeotropic mixture with water, and fractional distillation.

3 Claims, 1 Drawing Figure

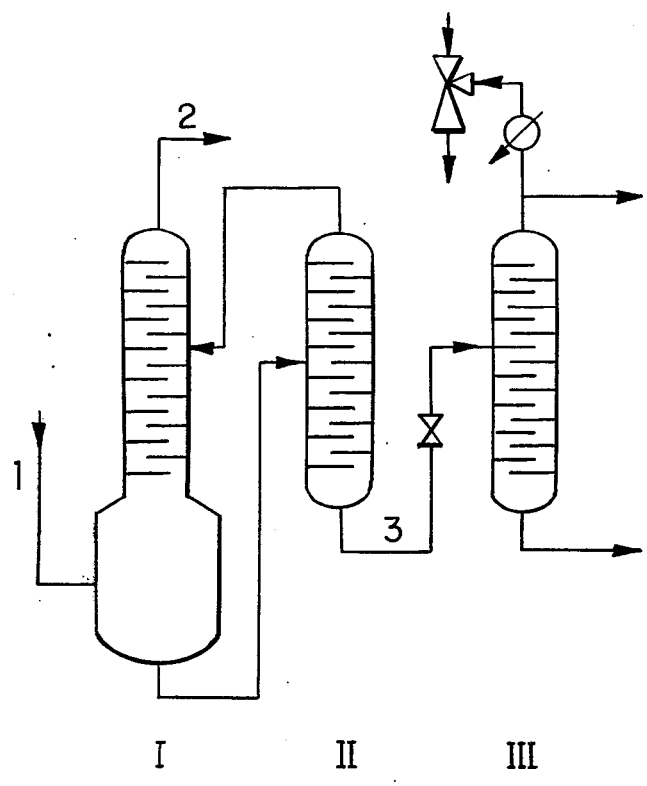

MANUFACTURE OF SUCCINIC ANHYDRIDE

The present invention relates to a process for the manufacture of succinic anhydride by eliminating water from succinic acid using a chemically inert hydrophilic solvent which does not form an azeotropic mixture with water, and fractional distillation. The resulting reaction is complete and gives a pure product.

It is known that aromatic ortho-dicarboxylic acids and aliphatic 1,2- and 1,3-dicarboxylic acids form cyclic anhydrides spontaneously, e.g. on prolonged heating, with elimination of water from the molecule. However, to achieve a complete reaction, the preparative technique is usually to employ water-dissociating agents such as phosphorus oxychloride, acetyl chloride or thionyl chloride. On account of their cost, these auxiliaries are usually unsuitable for large-scale production of cyclic anhydrides.

The spontaneous dehydration of succinic acid to form succinic anhydride usually occurs at a temperature of about 200°C, which must be raised to up to 250°C to complete the elimination of water. At temperatures between 200° and 250°C the vapor pressure of succinic acid reaches a point at which considerable amounts thereof sublime and cause heavy incrustations on stirrers and fittings. The water formed during the reaction acts in the same manner by effecting carrier steam distillation. Thus it is very difficult to manufacture succinic anhydride on an industrial scale.

Attempts have also been made to separate the succinic anhydride from the mixture of succinic acid and its higher homologs with the avoidance of the above difficulties by adding a hydrophobic solvent to the mixture of substances. During distillation, the thus reduced water vapor partial pressure of the system shifts the equilibrium of the reaction toward completion of anhydride formation. The entire vapor phase is condensed as a whole and the water is separated in a trap and the solvent is recycled. On account of the necessarily low solvent action of the hydrophobic solvent on succinic acid and its anhydride — a prerequisite for carrier vapor distillation —, only a small portion of the solids precipitated by condensation is redissolved. This means, however, that in this case also incrustations occur in the vapor portion of the apparatus, i.e. the portion leading from the evaporator to the water trap, which in turn makes it impossible to operate the plant for a relatively long period without trouble occurring.

It is an object of the invention to provide a process which avoids the undesirable phenomena caused by sublimation and carrier vapor distillation and which permits trouble-free continuous operation.

We have found that succinic anhydride may be obtained by dehydrating succinic acid without the occurrence of the above drawbacks by heating succinic acid with a chemically indifferent hydrophilic solvent having a high solvent action on succinic acid and its anhydride and a condensation temperature between 100° and 235°C and preferably between 185° and 210°C and which does not form an azeotropic mixture with water, to the boil, condensing the resulting vapors in a fractionating column, removing the water formed overhead and separating the resulting succinic anhydride from the solvent by distillation.

This process not only achieves complete water elimination but also makes trouble-free continuous operation possible.

The indifferent organic solvent must have definite hydrophilic properties. These may be defined as a minimum solubility of one part of water per part of solvent at 100°C and atmospheric pressure. Moreover, succinic acid and succinic anhydride must also show good solubility therein, i.e. the solvent should dissolve at least one part of succinic acid in ten parts of solvent at 100°C. Furthermore, the condensation temperature must be between that of water and that of succinic acid without an azeotropic mixture being formed with water. The aforementioned temperature range of from 100° to 235°C represents standard conditions.

Suitable solvents may be selected e.g. from the groups comprising cyclic lactones of hydroxycarboxylic acids, glycol ethers, glycol esters and glycol etheresters and acetals. They generally have molecular weights between 60 and 250.

Although all organic solvents having the aforementioned properties are suitable for the process of the invention, the following solvents represent a particularly advantageous selection: butyrolactone, valerolactone, diglycol diethyl ether, glycol diacetate, acetaldehyde butyl acetal and glycol monobutyl ether acetate.

The fractional distillation is carried out in a fractionating column having a medium number of trays suitable columns, for example, have a separating efficiency of from 10 to 100 theoretical trays. In this manner, stepwise condensation of the liquids with reflux causes separation of water from the succinic acid or succinic anhydride.

The amount of solvent included in the system should advantageously be such that adequate reflux thereof into the column during distillation is ensured, e.g. a reflux of at least 10% by weight. The process places no upper limit on the content of solvent. Suitable amounts of solvent are thus in the range of 30% of the reaction mixture or more, preferably from 100 to 1000%.

At the commencement of distillation the temperature at the top of the column is adjusted so as not to exceed 100°C. This means that the water produced by anhydride formation, together with any water already present in the mixture, forms the distillate. The solvent condensed in the middle portion of the column brings the succinic acid and its anhydride back to the bottom in dissolved form. In this way, no undesirable incrustations are formed over the entire apparatus. When the water elimination is substantially complete, preferably to an extent of about 90%, there is no longer sufficient water for removal and reflux. This means that the transition temperature at the top of the column rises and the distillate now contains some of the organic solvent of the system.

One way of stopping the process would be, at this point, to set the column to total reflux until the said residual water has collected at the top of the column and can be removed at the transition temperature of 100°C.

A more advantageous method is to continue distillation and collect the water/solvent and solvent/water mixture thus obtained together with the main solvent fraction and the first runnings of solvent/succinic anhydride and to add the next batch thereto or to operate the entire process continuously by conventional means.

Distillation commences at atmospheric pressure and is finally continued at a pressure of less than 100 mm Hg and preferably at about 45 mm Hg. The succinic anhydride formed may be distilled over in a pure state, preferably at about 170°C/45 mm Hg, following the distilled solvent. The yield of anhydride, based on succinic acid used, is at least 90% and its purity is higher than 95%.

The continuous form of the dehydration is particularly advantageous, since it makes it possible to recycle the solvent. The general set-up is that shown in the accompanying drawing. Dehydration and overhead separation of water 2 occur in column I. The feed of succinic acid which may or may not have a moisture content, and the conditions of fractionation are advantageously controlled so as to give a residence time of from 2 to 6 hours in this column. In the distillation column II the solvent is separated at atmospheric or slightly subatmospheric pressure and the resulting melt 3 of crude anhydride is purified in column III by vacuum distillation.

The succinic acid to be dehydrated may be aqueous or dry. However, it is also possible to dehydrate the succinic acid in admixture with other dicarboxylic acids such as glutaric acid and adipic acid and then to obtain the pure anhydride by distillation. Mixtures of such dicarboxylic acids are produced, for example, in the industrial synthesis of adipic acid by oxidation of cyclohexanol.

The process of the invention is illustrated with reference to the following Examples.

EXAMPLE 1

A mixture of 2000 g of succinic acid (water-wet, 82.5%) and 400 g of butyrolactone is heated to the boil in a fractionating column having 10 theoretical trays. The rising vapor is removed at a reflux ratio of 3:1 and is condensed. The bottoms temperature is initially 115°C and rises over 4 hours at a constant rate to 170°C. The temperature at the top of the column remains at 100°C during this period and 500 g of water are distilled off. The reflux ratio is now raised to 5:1. After a further hour a total of 560 g of water has distilled off. The temperature of the vapors at the top of the column rises to 200°C and dehydration is complete. The butyrolactone is distilled off at 110°C/35 mm Hg to give 392 g thereof. The vacuum is then increased to 17 mm Hg and an intermediate run of butyrolactone/succinic anhydride gives a total of 54 g distilled off. At a constant boiling temperature of 142°C, 1094 g of succinic anhydride then distil over, this being equivalent to 78% of theory.

The resulting succinic anhydride has a solidifying point of 118°C. It has a pale yellow color and may be made substantially colorless by repeating the vacuum distillation. The yellow content of a 5% solution in methanol is 2, as measured by APHA. The content of succinic anhydride is 97%, as determined chromatographically.

EXAMPLE 2

1000 g of succinic acid (water-wet, 92%) are heated to the boil with 400 g of butyrolactone in a fractionating column. Water is removed overhead. The bottoms temperature rises from 160° to 200°C. Slight vacuum (about 100 to 300 mm Hg) is applied and controlled so as to maintain the boiling temperature of the bottoms at a constant value of 200°C. The transition temperature of the water is between 80° and 90°C and rises suddenly, after 3.5 hours, to 130°C. The receiver is now changed and the distillate is water-containing butyrolactone. At a temperature of from 160° to 165°C, 383 g of butyrolactone are recovered. The succinic anhydride formed is obtained at an increased vacuum (45 mm, boiling temperature 170°C) in an amount of 623 g, equivalent to 80% of theory. The solidifying point is 118°C and the anhydride content is 97%. The residue weighs 84 g.

In a repetition of the test, this residue is used, together with redistilled butyrolactone made up to 400 g, for renewed anhydridization of 1000 g of moist succinic acid. The anhydride yield over both tests is then 89% of theory.

EXAMPLE 3

1000 g of succinic acid (water-wet, 80%) are heated to the boil with 300 g of diglycol diethyl ether in a fractionating column. Pure water is obtained at the top of the column. Some of this water is refluxed into the column and the remainder is removed. The bottoms temperature rises to 210°C over 3 hours. The solvent is then distilled off under reduced pressure, followed by the succinic anhydride, also under reduced pressure.

We claim:

1. In a process for the production of succinic anhydride by dehydration of succinic acid the improvement which comprises heating succinic acid with a hydrophilic solvent selected from the group consisting of butyrolactone, valerolactone, diglycol diethyl ether, glycol diacetate, acetaldehyde butyl acetal, and glycol monobutyl ether acetate, to the boil, condensing the resulting vapors in a fractionating column, removing the water formed overhead and separating the resulting succinic anhydride from the solvent by distillation.

2. A process as claimed in claim 1 wherein succinic acid is continuously fed to the bottom of a first fractionating column containing the solvent used and in which the mean residence time is from 2 to 6 hours, the water is distilled overhead, the bottoms are supplied to the middle portion of a second fractionating column, and the solvent is distilled overhead and recycled to said first column.

3. A process as claimed in claim 2 wherein the bottoms of said second column are redistilled.

* * * * *